United States Patent [19]

Wright et al.

[11] 4,182,890

[45] Jan. 8, 1980

[54] ETHYL 2-OXO-3-PHENYLETHYLAMINOPIPERI-DINE-4-CARBOXYLATE HYDROCHLORIDE

[75] Inventors: George C. Wright; Ronald E. White, both of Norwich, N.Y.

[73] Assignee: Morton-Norwich Products, Inc., Norwich, N.Y.

[21] Appl. No.: 967,365

[22] Filed: Dec. 7, 1978

[51] Int. Cl.² .......................................... C07D 211/76
[52] U.S. Cl. ................................... 546/221; 424/267; 546/242; 546/297
[58] Field of Search ........................................ 546/221

[56] References Cited

U.S. PATENT DOCUMENTS

| 3,186,991 | 6/1965 | Ohnacker | 546/221 |
| 3,511,844 | 5/1970 | Plostnieks | 546/221 |

FOREIGN PATENT DOCUMENTS

| 98811 | 3/1961 | Netherlands | 546/221 |

Primary Examiner—Alan L. Rotman
Assistant Examiner—Richard A. Schwartz
Attorney, Agent, or Firm—Anthony J. Franze

[57] ABSTRACT

Ethyl 2-oxo-3-phenylethylaminopiperidine-4-carboxylate hydrochloride is useful as a muscle relaxant.

1 Claim, No Drawings

ETHYL 2-OXO-3-PHENYLETHYLAMINOPIPERIDINE-4-CARBOXYLATE HYDROCHLORIDE

This invention relates to the chemical compound ethyl 2-oxo-3-phenylethylaminopiperidine-4-carboxylate hydrochloride. It possesses pharmacologic activity. Particularly, it exhibits skeletal muscle relaxant activity when administered to warm blooded animals. Upon intravenous administration of it to rats in a dose of about 25 mg/kg, inhibition of gastrocnemius muscle twitch is elicited. Suitable vehicles for intravenous administration include physiologically acceptable menstrua such as dimethylsulfoxide, tetrahydrofuryl alcohol and dimethylacetamide.

The compound of this invention can be readily formulated into pharmaceutical compositions such as tablets, elixirs, solutions, suspensions, capsules and the like using excipients and adjuvants commonly employed for such purposes and with which there is no incompatibility.

In order that this invention may be readily available to and understood by those skilled in the art, the following method of preparing it is described:

A. Ethyl 2,3-Dioxo-4-piperidinecarboxylate

A few crystals of iodine and a small amount of $Hg_2Cl_2$ were introduced into a mixture of benzene (2 liters) and ethanol (280 ml). Sodium methoxide (108 g, 2.0 moles) was added with stirring. A mixture of 2-pyrrolidone (17.2 g, 2.0 moles) and diethyl oxalate (292 g, 2.0 moles) was introduced in large increments. Slight exothermicity was observed. The reaction mixture was refluxed for 24 hours. It was acidified with 320 ml of 1:1 HCl. The hot benzene was decanted, the salt and water were mixed with fresh boiling benzene, and the benzene was decanted. This extraction with boiling benzene was done three times. The extracts were combined and filtered by gravity. The filtrate was concentrated under reduced pressure to approximately 1.5 liters. This was concentrated on a steam bath to approximately 600 ml. On cooling overnight, a solid (151 g, m.p. 148–151°) was obtained. Yield: 40.7%.

B. Ethyl 2-Oxo-3-(phenethylimino)isonipecotate

A mixture of A (185 g, 1.00 mole) and toluene (2000 ml) was treated with phenethylamine (133 ml, 1.05 mole) with mechanical stirring; the addition was slightly exothermic and the reaction mixture became thick. The mixture was treated with conc. HCl (0.5 ml) and gradually heated to reflux over 2 hours. The reaction solution was refluxed (using a Dean-Stark trap) for 5.5 hours, and $H_2O$ (19 ml) was collected. The cooled (25°) solution was filtered to remove a small amount of white solid, and the filtrate was stripped of solvent under the water pump. Trituration of the semi-crystalline, cooled residue in ether (300 ml), with storage in the refrigerator overnight, gave light yellow crystals. The product was collected, washed with ether ($7 \times 25$ ml) and dried in air overnight; yield: 246 g (85%). Recrystallization of product (70 g) from benzene (total solution volume of 100 ml) gave crystals, m.p. 99–100°, yield: 56 g (68%).

Anal. Calcd. for $C_{16}H_{20}N_2O_3$: C, 66.65; H, 6.99; N, 9.72. Found: C, 66.47; H, 6.98; N, 9.69.

C. Ethyl 2-Oxo-3-(phenethylamino)isonipecotate Hydrochloride

A mixture of B (60 g, 0.21 mole), $CH_3OH$ (400 ml), and 5% Pd/C with 50% $H_2O$ (25 g) was subjected to hydrogenation at room temperature for 28 hours. The reaction mixture was filtered of the catalyst, and the filtrate was concentrated under reduced pressure to a volume of 100 ml, with a bath temperature of 45–50°. The resultant solution was treated with a solution of dry HCl-isopropanol (50 ml) with cooling in an ice bath. After dilution with anhydrous ether (100 ml) the white, crystalline hydrochloride was collected; m.p. 215–217°, yield: 41 g. The product (41 g), combined with an additional 32 g from a second run, was recrystallized from ethanol (800 ml); m.p. 223–225°, yield: 45 g (37%).

Anal. Calcd. for $C_{16}H_{22}N_2O_3 \cdot HCl$: C, 58.80; H, 7.09; N, 9.57. Found: C, 58.40; H, 6.92; N, 8.74.

What is claimed is:
1. The compound ethyl 2-oxo-3-phenylethylaminopiperidine-4-carboxylate hydrochloride.

* * * * *